(12) United States Patent　　(10) Patent No.: US 7,104,420 B2
Maffei　　(45) Date of Patent: Sep. 12, 2006

(54) DISPENSING BOX FROM WHICH ITEMS CAN BE SLID OUT

(75) Inventor: Camilla Maffei, Pistoia (IT)

(73) Assignee: PROJECT S.a.s. di Massimo Menichelli & C., (IT)

( * ) Notice: Subject to any disclaimer, the term of this patent is extended or adjusted under 35 U.S.C. 154(b) by 38 days.

(21) Appl. No.: 10/505,636

(22) PCT Filed: Dec. 9, 2003

(86) PCT No.: PCT/IT03/00809

§ 371 (c)(1),
(2), (4) Date: Aug. 19, 2004

(87) PCT Pub. No.: WO2004/054884

PCT Pub. Date: Jul. 1, 2004

(65) Prior Publication Data

US 2005/0115869 A1　　Jun. 2, 2005

(30) Foreign Application Priority Data

Dec. 13, 2002　(IT) ............................. FI2002A0250

(51) Int. Cl.
*A61B 19/08*　(2006.01)
*B65G 59/00*　(2006.01)
*A47F 1/04*　(2006.01)

(52) U.S. Cl. .................... 221/92; 206/440; 221/309; 221/305

(58) Field of Classification Search ................... 221/92, 221/123, 124, 252, 58, 305, 309, 117; 206/440, 206/438, 39.3, 39.5, 39.6; 209/39.3
See application file for complete search history.

(56) References Cited

U.S. PATENT DOCUMENTS

| 1,173,843 | A | * | 2/1916 | Morten | .................. 206/39.3 |
| 1,173,848 | A | * | 2/1916 | Morten | .................. 238/205 |
| 3,185,373 | A | * | 5/1965 | Margulies | .................. 221/123 |
| 2004/0149771 | A1 | * | 8/2004 | Maffei | .................. 221/305 |

FOREIGN PATENT DOCUMENTS

DE　　　1 225 541　　9/1966
WO　WO 02/094686　　11/2002

* cited by examiner

*Primary Examiner*—Gene O. Crawford
*Assistant Examiner*—Timothy Waggoner
(74) *Attorney, Agent, or Firm*—McGlew & Tuttle, PC

(57) ABSTRACT

The inside of the box is divided into two seats by an inclined separator (F) that ends at two opposing sliding-out slits. The main faces (A, B) have two slits (A1, A2, B1, B2) and the separator (F) has a slit (N) parallel to the direction in which the items can be slid out. Two arms (L, L2; M, M2) are housed and secured in said slit (N) and their width is such that they reach said two main faces (A, B). In this way the inside of the box is divided into four spaces (two for each of the faces A and B) for identical or different items.

11 Claims, 5 Drawing Sheets

DISPENSING BOX FROM WHICH ITEMS CAN BE SLID OUT

Use has long been made of boxes (usually made of paperboard) of various dimensions containing plasters of different shapes (rectangular, round etc.), sizes and colors for covering and protecting small wounds and abrasions of the skin. Boxes of this type can also be filled with plasters of different types, such as non-woven plasters (or of other material), wrappers for disposable hygienic protection of the doctor's stethoscope/fonendoscope, individual wrappers for tongue depressors, individual wrappers for spatulas and cervical brushes for gynecological use. Similar boxes can also contain other products or objects of limited thickness and of at least moderate bending resistance, provided if necessary by the individual protection of each object. For simplicity's sake this text will refer to plasters. The use of plasters (individually wrapped) of any kind, shape and size—even contained loose in one box—has become routine in clinics and hospitals, in doctors' bags, but also in homes, schools and cars as part of the first-aid kit.

In an earlier exclusive right belonging to the same proprietor, the boxes containing the plasters or other objects were modified to achieve certain advantages, first and foremost that the box can be used without having to open it every time a plaster needs to be removed. The box thus becomes a dispensing box.

The dispensing box of the previous exclusive right also allows the user to choose, from the outside, which type of plaster to remove, because the box can for example dispense plasters all of one size (or all of one kind) but also of two or three sizes, kinds and/or different shapes. The user can immediately see from the outside what plasters are still available for use without having to open the pack and empty the content in order to find the most suitable one for the need of the moment and then, having selected the plaster, putting all the others back into the pack.

The dispensing box of said previous exclusive right, which can be made from pieces of paperboard blanked and with ordinary "fold and glue" lines and therefore be easily produced industrially, comprises in at least one of the two main faces a window and in the internal volume of the box a wall whose surface is inclined with respect to said main face; said wall and said face define a slit through which an individual item can be slid out by acting on it through said window. In one embodiment of the previous exclusive right, the box comprises in each of the at least one window in the two main faces and, in the internal volume of the box, a separator forming an inclined plane with respect to said two main faces and defining with said two faces two respective opposed seats for items and two opposed slits, through each of which an individual item can be slid out by acting on it through the corresponding window. Said separator may be formed as an extension of one of the two faces at right angles to the slits.

A box according to the previous exclusive right comprises, in another version, on one of the main faces, two adjacent windows and then includes, in the corresponding seat, an internal divider between the two windows, to form in said seat two separate spaces for different items to be removed through the respective slit. Said internal divider may consist of two arms continuing from two opposite edges perpendicular to one of the two faces and to one of the slits, which arms are folded along the internal wall of the box contiguous to the slit and inwards into said seat to form said internal divider and to define said two separate spaces.

The subject-matter of the present invention is improved ways of obtaining a greater number of separate spaces for items, of making the internal dividers more stable, and of achieving other purposes which will become clear as the text proceeds.

In a box of the abovementioned kind according to the present invention:
said separator has at least one slit parallel to the direction in which the items are to be slid out;
at least one of said tab arms is received and secured in said slit and its width is such that it reaches both of said main faces, in order to divide each of said two seats—located between the separator and each of the two main faces—into at least two spaces for identical or different items.

In one possible embodiment, both tab arms are received in one and the same slit, thus producing a total of four separate spaces. In another possible embodiment, said separator has two slits, and said two tab arms are housed each in the slit nearest to the edge to which the said arm is attached, thus giving a total of six separate spaces.

Advantageously, each tab arm ends in a fork that engages on the end of the slit in which the arm is housed.

In another possible embodiment of this invention, where said separator is formed as an extension of one short side and one of said two main faces, at least one of the long sides of the box has reading windows, and furthermore between said long side and the contiguous inclined edge of the separator a slider is housed in such a way that it can be slid, one of its said ends projecting on the side of said short side so that the slider can be moved in and out to allow information contained on the slider to be read through said reading windows. Two independent sliders can also be provided on the inside of the two long sides, both with windows.

A clearer understanding of the invention will be gained from the perusal of the description and the accompanying drawing, the latter showing a practical, non-restrictive example of said invention. In the drawing:

FIGS. 8, 9, 10 and 11 show another alternative embodiment, in the outline of the blank, in perspective, of the complete box and in section on XI—XI as marked in FIG. 10.

FIGS. 1–4 show the outline of the blank for a box that provides four spaces for items (such as one or more sizes of plaster), before it is folded and glued to form the dispensing box.

Letters A and B denotes the two main faces, A being bounded by fold lines or creases X, X1 and X2, and B being bounded by creases Y and Y1. Face A has two windows A1 and A2 while B has two windows B1 and B2. Beyond the crease X there extends a long side D and between the creases X1 and Y extends the long side C, opposite side D. Beyond crease Y1 extends a tab D1 for gluing to the inside surface of long side D. Beyond crease X2 extends a short side E, which is also bounded by a half-cut fold line E1, from which there extends a separator F in the form of an extension of face A and of short side E, with which it is aligned. Said separator F is further bounded by a crease X3 which, together with a parallel crease X4 defines a wall G of the box opposite short side E. Beyond the crease X4 extends a tab H for this closure. There are also two shaped tab arms L and M beginning at respective fold lines Z and Z1 which define long sides D and C. Each of said tab arms L and M is divided by a fold line L1, M1, respectively, which defines an extension L2, M2, respectively, these last being designed to create an internal divider. These two extensions L2 and M2 have a width approximately equal to the width of long sides D and C and hence to the thickness of the folded box and to the distance between the two faces A and B. Moreover, each of these extensions L2 and M2 ends in a fork L3 and M3.

The separator F contains a slit N which is wider at N1 towards crease X3 and ends in a cusp N2.

To form the box, the first operation is to fold the separator F along the half cut E1 and the crease X2, bringing the separator F over until it touches the inside of face A of the box. Crease Y is then folded, then crease X to glue side D to the tab D1. The dispensing box is thus formed by the six sides A, B, C, D, E and G and can assume the form of a parallelepiped, with separator F contained inside it. The windows A1, A2, B1, B2 (formed on the respective sides A and B) will allow the plasters or other items to be removed one at a time.

Figure 1:
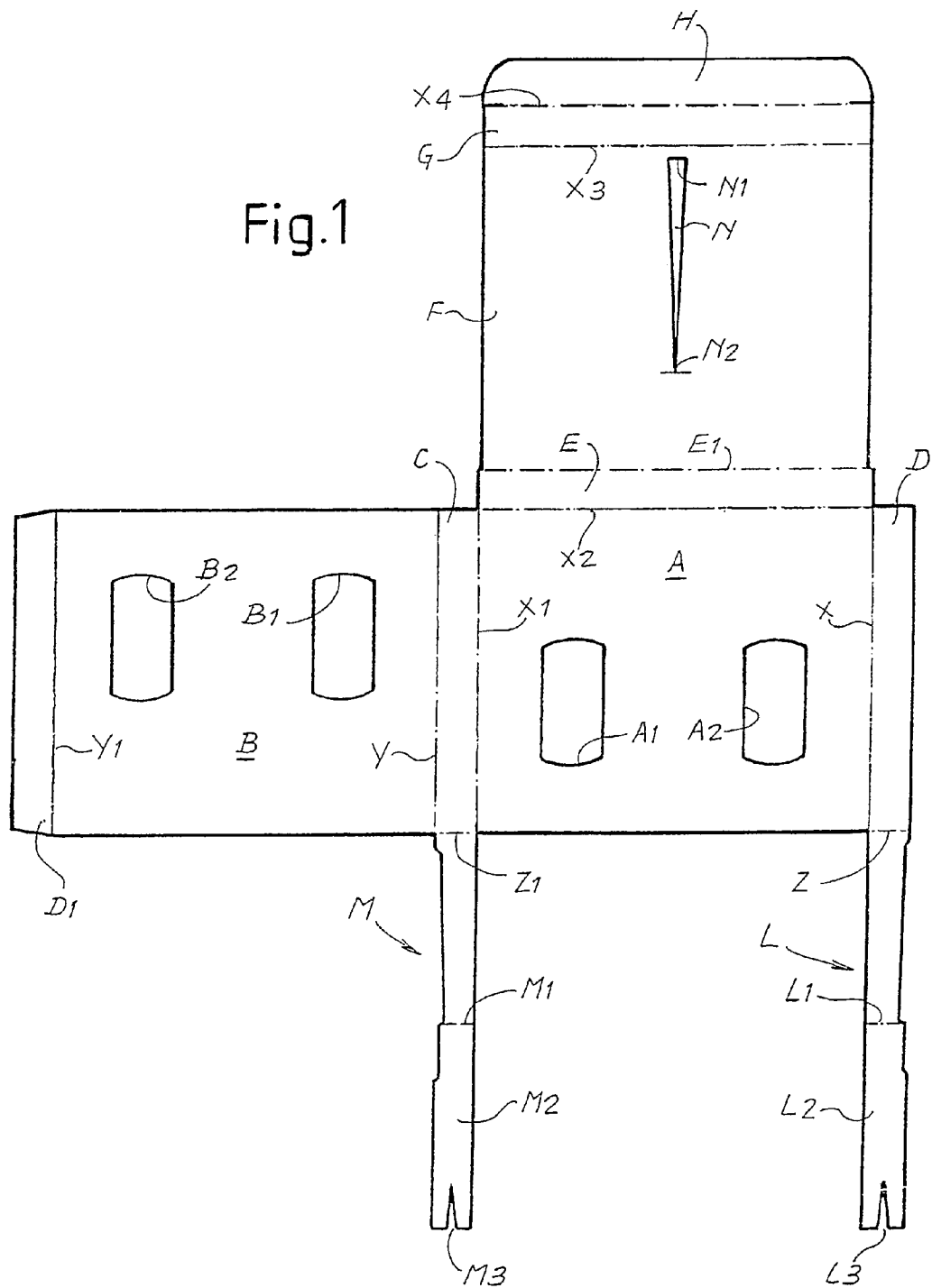
FIG. 1 shows the outline of a blanked sheet element for forming a box with four seats for items to be packaged and removed individually.
Figure 2:
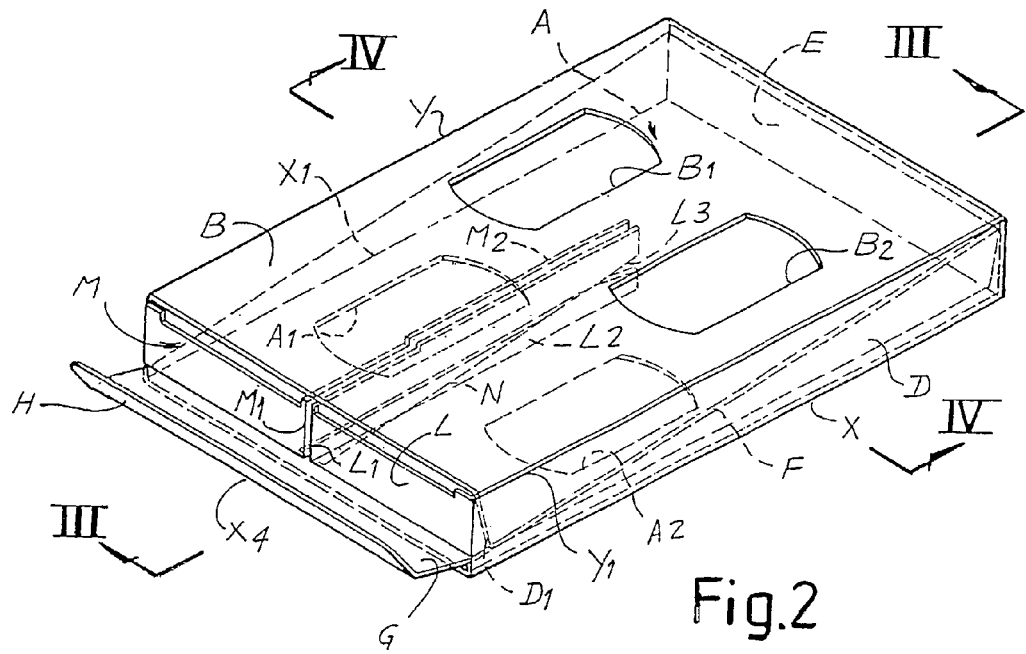
FIGS. 2, 3 and 4 show a perspective view of the box almost completely closed, and sections on III—III and IV—IV as marked in FIG. 2.
Figure 3:
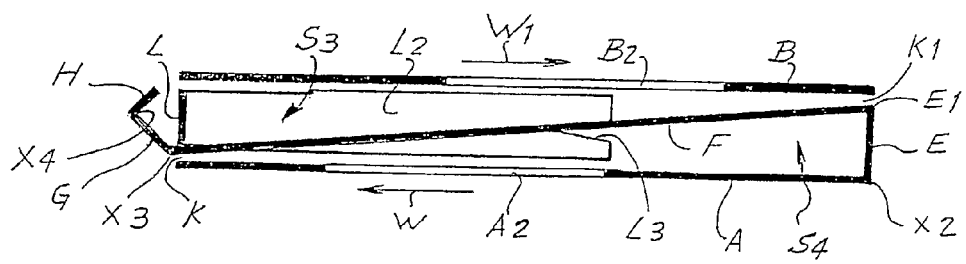
Figure 4:
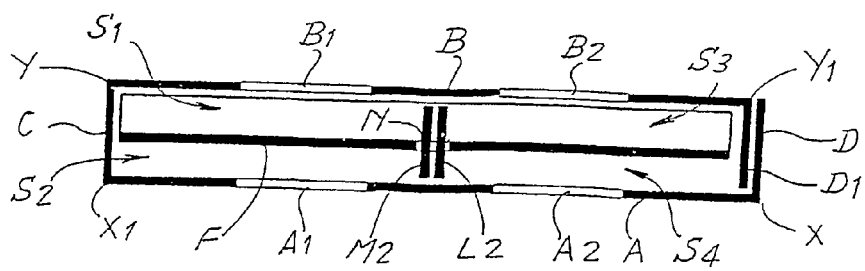
Figure 5:
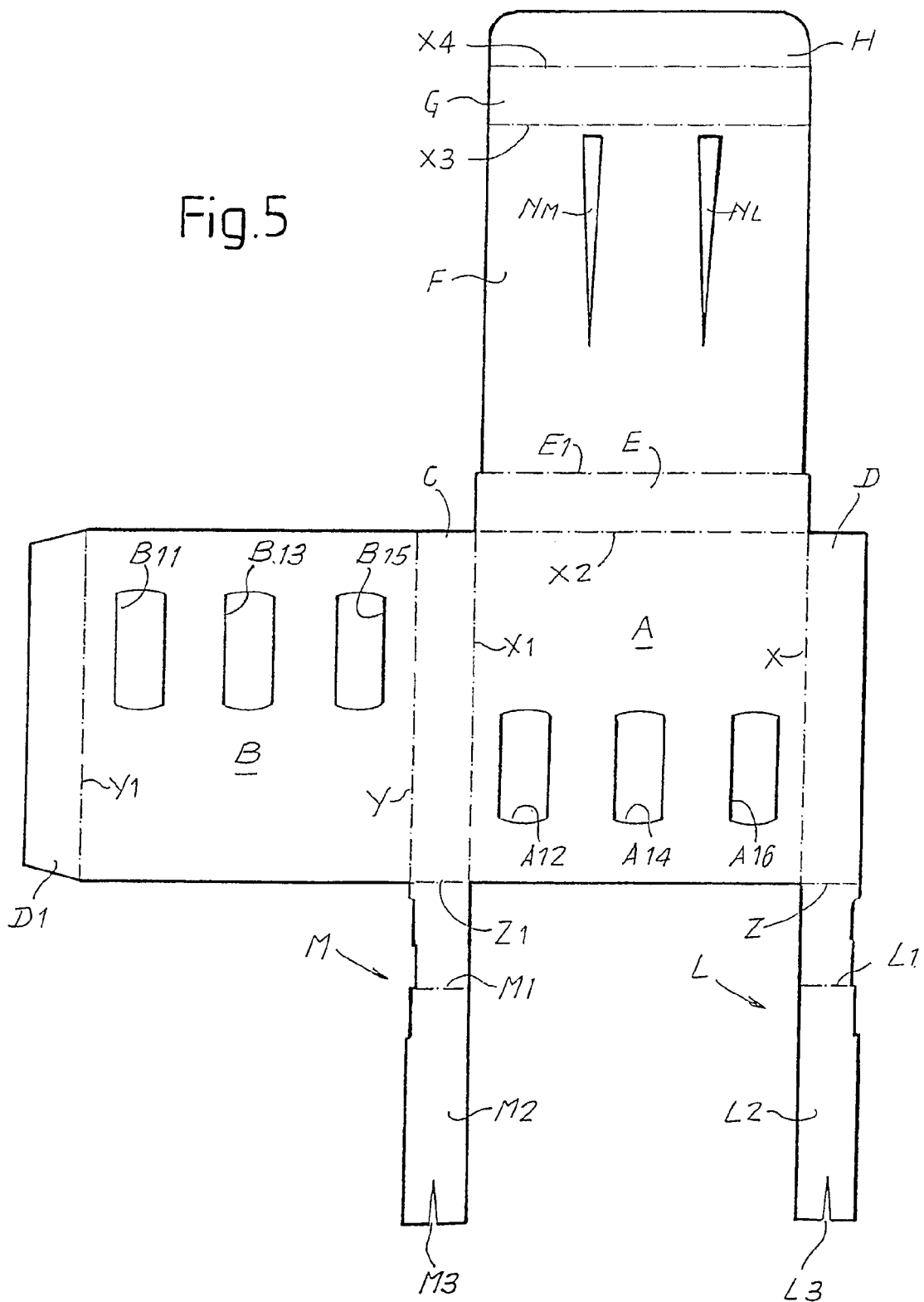
FIGS. 5–8 show, in a similar way to FIGS. 1–4 an alternative embodiment, in the outline of the blank, in perspective and in sections on VII—VII and VIII—VIII as marked in FIG. 6.
Figure 6:
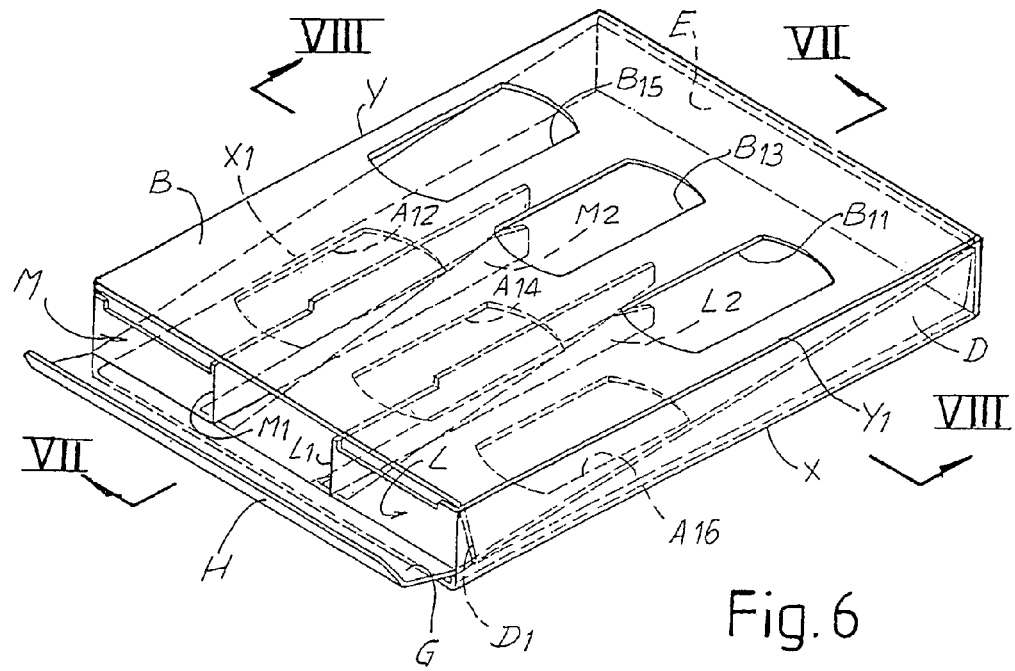
Figure 7:
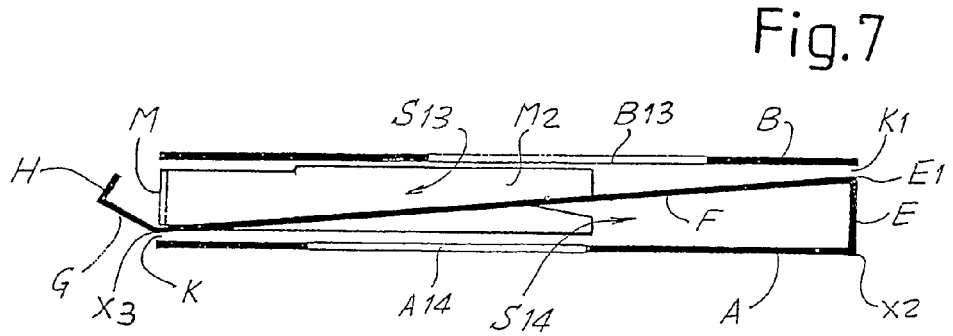

Once the box is securely in its three-dimensional form (FIGS. 2–4) in which it is stabilized by short side E, the four sets of items (such as plasters individually wrapped in wrappers usually of paper but also of other materials) can be inserted. Each set may consist of for example six/eight or more plasters, depending on the dimensions and shape of the dispensing box and on the dimensions of the various types of plaster (or other items). These sets of items can be introduced through side G, which is kept open for this purpose, into the internal spaces defined between the separator F and faces A and B, behind windows A1 and A2 and then, after moving the separator F, behind windows B1 and B2. The tab arms L and M are then folded along their creases Z, L1 and Z1, M1, and their adjacent extensions L2 and M2 are inserted into the box inside the slit N in such a way that end forks L3, M3 engage over the cusp N2 of the slit N. In this way four spaces S1 to S4 are created (see FIG. 1) for the four sets of items, thus fulfilling the function of keeping separate from each other the two sets of items located behind windows A1 and A2 in face A, and also the two sets of items located behind the two windows B1 and B2 in face B. The different sets of plasters separated by the tabs L and M and by the separator F cannot therefore become mixed up together and thus enable correct operation and selection. Once the box is closed by the wall G and the flap H, the dispenser is ready to be used.

It is possible to select an item contained in the space behind window A1 of face A, or an item contained in the space behind window A2, or an item contained in the space behind window B1 or window B2. By inserting a finger through one of the windows A1, or A2, or B1, or B2, it is possible to slide the selected item along the space defined by the inclined plane formed by the separator F, so as to push (one at a time) out through the slit K (FIG. 3) the item corresponding to window A1, or window A2 in sliding direction W, or out of slit K1 corresponding to window B1 or window B2 in face B, in sliding direction W1. Slit K is formed along the edge between crease X3 and face A, while slit K1 is formed along the edge between crease E1 and face B. The slits K and K1 are both made of suitable dimension for the thickness of the plaster or other item which it is intended to remove. Slit K (from which the plasters visible in window A1 or A2 are removed one at a time) and slit KI (from which the plasters visible in windows B1 and B2 are removed one at a time) are created by the correct erection of the dispensing box, the measurements and dimensions of which are defined precisely in order to form these narrow slits between sides A and G, and sides B and E, respectively, allowing the plaster to be pushed out even while all sides of the dispensing box are kept closed. Slits defined between face B and the arms L, M allow the tab H to be inserted here, thereby completing the closure of the box. The slits K and K1 remain available for removal of whichever item may be desired when the latter are acted upon through the windows A1 or A2 or B1 or B2.

Figure 8:
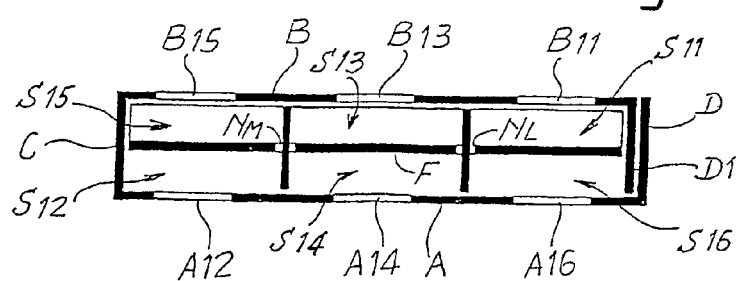

In the alternative embodiment shown in FIGS. 5–8, six spaces S11–S16 are formed (rather than four spaces S1–S4 as in the example shown in FIGS. 1–4) for six sets of items, such as plasters or the like. In this alternative embodiment the reference numbers are the same as in the previous example. The alternative embodiment involves forming two slits NM and NL in the separator, and the two tab arms L and M have the creases L1 and M1 positioned in such a way that the extensions L2 and M2 fit into the corresponding slit NL and NM. The six spaces S11, S13, S15, S12, S14 and S16 are thus defined as seen in FIG. 8, and correspond to windows B11, B13 and B15 and A12, A14 and A16.

Figure 9:
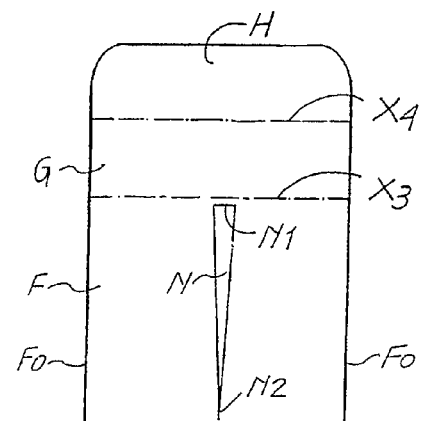
Figure 10:
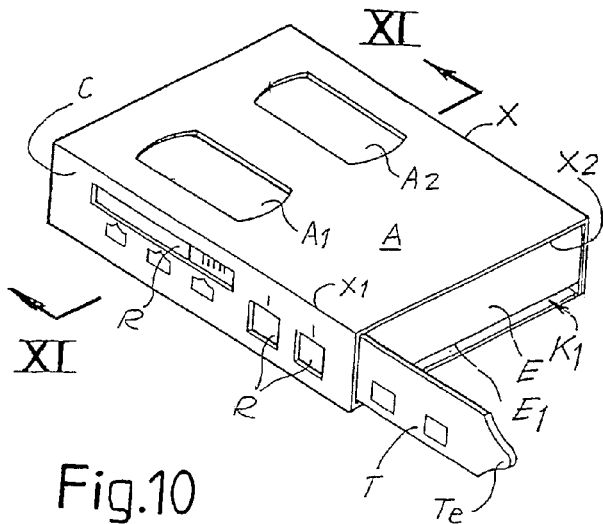
Figure 11:
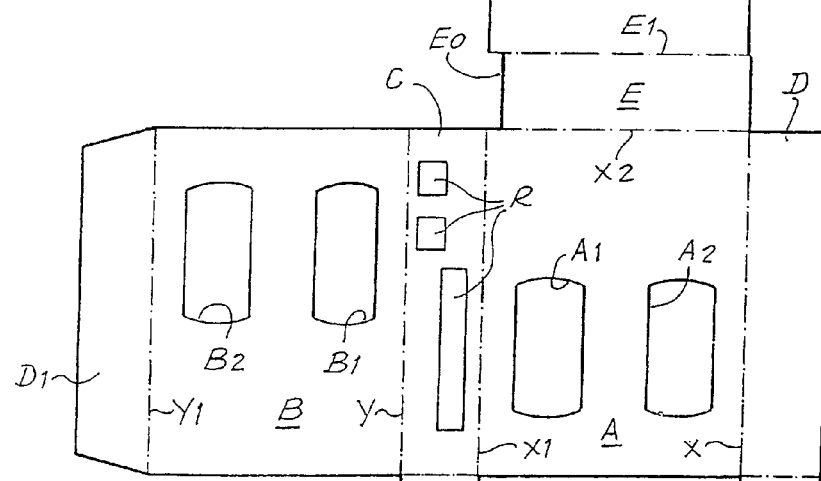
Figure 11:
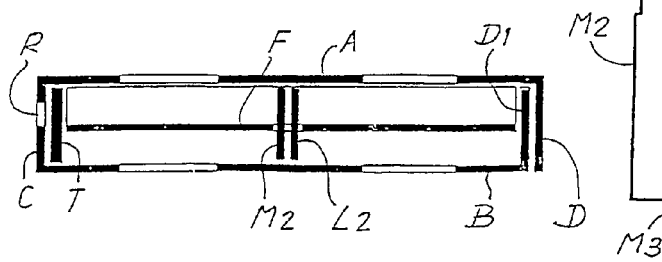

FIGS. 9, 10 and 11 illustrate an alternative embodiment to the examples shown in FIGS. 1–4, using the same reference numbers. In this alternative embodiment, independently of the number of spaces available inside the box, windows R are formed in long side C (and/or in long side D and correspondingly in tab D1) also, short side E is given a depression Eo at the corresponding end adjacent to long side C (and/or D+D1). A thin slider T is also provided and fits between the inside surface of long side C (and/or of long side D) and the corresponding lateral edge Fo of the separator F. Slider T has an end Te that projects from the edge between long side C and short side E so that the slider T can be pushed in and out so that the information on it can be consulted through the windows R.

Doubling the provision of the slider inside the long sides C and D+D1, increases the amount of information that can be consulted on them.

It will be understood that the drawing shows only an illustrative embodiment provided purely as a practical demonstration of the invention, which invention can be varied in its shape and arrangements without thereby departing from the scope of the concept on which the innovation is based. The presence of any reference numbers in the appended claims is for the purpose of facilitating the reading of the claims with reference to the description and drawing, and does not limit the scope of protection represented by the claims.

The invention claimed is:

1. A parallelepiped box made of board or the like for the packaging and dispensing of items, the box comprising:
   a first main face with windows;
   a second main face with windows; end walls;
   side walls, said first main face being spaced from said second main face and cooperating with said side walls and said end walls to define an internal volume of the box;
   a separator forming an inclined plane with respect to first main face and said second main face and defining with said first main face and said second main face two respective opposed seats for items, said end walls forming with said first main face and second main face opposed dispensing slits, through each of which an individual item can slide out by acting on the item through the corresponding window;

an internal divider to form in one of said two seats two separate spaces for different items to be removed through the corresponding dispensing slit, said internal divider including two tab arms continuing from two opposite edges perpendicular to said first main face and second main face, said tab arms being folded to form said internal divider and to define said two separate seats, said separator being formed as an extension of one of the first main face and second main face with a portion of said extension being at a right angle to said dispensing slits, said separator having a separator slit parallel to a direction in which the items are to be slid out, at least one of said tab arms being received and secured in said separator slit and having a width such that said at least one of said tab arms reaches each of said first main face and said second main face and divides each of said two seats, located between the separator and each of said first main face and said second main face, into at least two spaces.

2. A box according to claim 1, wherein each of said tab arms is received in said separator slit.

3. A box according to claim 1, wherein said separator has a second separator slit and said tab arms are housed each in one of said separator slit and said second separator slit that is nearest to an edge to which said tab arms are respectively attached, whereby both seats are divided into three spaces.

4. A box according to claim 1, wherein each tab arm ends in a fork that engages on said separator slit or on a second separator slit and each tab arm forms a part of one of said walls.

5. A parallelepiped box for the packaging and dispensing of items a first main face with windows;

a second main face with windows;

short side walls;

long side walls, the first main face being spaced from the second main face and cooperating with said long side walls and short side walls to define an internal volume of the box;

a separator forming an inclined plane with respect to said two main faces and defining with said two faces two respective opposed seats for items, said end walls forming with said first main face and second main face opposed dispensing slits, through each of which an individual item can be slide out by acting on it through the corresponding window, said separator being formed as an extension of one of said short side walls and of one of said first main face and said second main face, said short side walls extending in a direction at right angles to the dispensing slits, one of said long side walls having reading windows;

a slider between said one of said long side walls and a contiguous inclined edge of said separator, said slider being housed to slide such that an end thereof can project from an end of one of said short side walls so that said slider can be moved in and out to allow information contained on said slider to be read through said reading windows.

6. A box according to claim 5, further comprising another slider independent of said slider, said another slider being disposed between another of said long side walls and a contiguous inclined edge of said separator, said another of said long side walls having reading windows whereby that said another slider can be moved in and out to allow information contained on said another slider to be read through said reading windows of said another of said long side walls.

7. A box according to claim 5, further comprising an internal divider to form in one of said two seats two separate spaces for different items to be removed through the corresponding slit, the internal divider including two tab arms continuing from two opposite edges perpendicular to the two faces, the tab arms being folded to form said internal divider and to define said two separate seats, said separator being formed as an extension of one of the first main face and second main face with a portion of the extension being at a right angle to the slits, said separator having a separator slit parallel to a direction in which the items are to be slid out, at least one of said tab arms being received and secured in said separator slit and having a width such that said least one of said tab arms reaches each of said first main face and said second main face and divides each of said two seats, located between the separator and each of said first main face and said second main face, into at least two spaces.

8. A parallelepiped box made of board or the like for the packaging and dispensing of items, the box comprising:

a first main face with windows;

a second main face with windows, said first main face being spaced from said second main face and cooperating to define an internal volume of the box;

a separator forming an inclined plane with respect to first main face and said second main face and defining with said first main face and said second main face two respective opposed seats for items, opposed dispensing slits being defined, through each of which an individual item can slide out by acting on the item through the corresponding window;

an internal divider to form in one of said two seats two separate spaces for different items to be removed through the corresponding dispensing slit, said internal divider including two tab arms continuing from two opposite edges perpendicular to said first main face and second main face, said tab arms being folded to form said internal divider and to define said two separate seats, said separator being formed as an extension of one of the first main face and second main face with a portion of said extension being at a right angle to said dispensing slits, said separator having a separator slit parallel to a direction in which the items are to be slid out, at least one of said tab arms being received and secured in said separator slit and having a width such that said at least one of said tab arms reaches each of said first main face and said second main face and divides each of said two seats, located between the separator and each of said first main face and said second main face, into at least two spaces.

9. A box according to claim 8, wherein each of said tab arms is received in said separator slit.

10. A box according to claim 8, wherein said separator has a second separator slit and said tab arms are housed each in one of said separator slit and said second separator slit that is nearest to an edge to which said tab arms are respectively attached, whereby both seats are divided into three spaces.

11. A box according to claim 8, wherein each tab arm ends in a fork that engages on said separator slit or on a second separator slit and each tab arm forms a part of side or end walls.

* * * * *